(12) United States Patent
Gosney et al.

(10) Patent No.: US 10,954,783 B2
(45) Date of Patent: Mar. 23, 2021

(54) EXTRACTION CLEANER AND GAS SYSTEM CHECK

(71) Applicant: Halliburton Energy Services, Inc., Houston, TX (US)

(72) Inventors: Jon Troy Gosney, Belville, TX (US); Mathew Dennis Rowe, Lafayette, LA (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 409 days.

(21) Appl. No.: 15/756,794

(22) PCT Filed: Oct. 22, 2015

(86) PCT No.: PCT/US2015/056949
§ 371 (c)(1),
(2) Date: Mar. 1, 2018

(87) PCT Pub. No.: WO2017/069765
PCT Pub. Date: Apr. 27, 2017

(65) Prior Publication Data
US 2018/0245466 A1    Aug. 30, 2018

(51) Int. Cl.
*E21B 49/00* (2006.01)
*E21B 21/00* (2006.01)
(Continued)

(52) U.S. Cl.
CPC .......... *E21B 49/086* (2013.01); *E21B 21/067* (2013.01); *G01N 1/2035* (2013.01);
(Continued)

(58) Field of Classification Search
CPC ... G01N 1/2035; E21B 49/086; E21B 21/067; E21B 34/00
See application file for complete search history.

(56) References Cited

U.S. PATENT DOCUMENTS 3,184,973 A    5/1965   Bradley
9,134,291 B2 *  9/2015  Jamison ............ G01N 33/2823
(Continued)

OTHER PUBLICATIONS

International Search Report and The Written Opinion of the International Search Authority, or the Declaration, dated Jul. 19, 2016, PCT/US2015/056949, 16 pages, ISA/KR.
(Continued)

*Primary Examiner* — Jamel E Williams
(74) *Attorney, Agent, or Firm* — Haynes and Boone, LLP

(57) ABSTRACT

Systems and methods for maintaining operation of gas sampling equipment utilized in oil and gas operations, wherein an isolation valve is deployed along a gas extraction conduit in order to isolate a gas analysis system from pressurized fluid that may be injected into the extraction conduit from a fluid delivery system. A parameter of the flow stream, such as a particular gas content or the presence of a bump gas, may be monitored. A change in the parameter may be indicative that debris is inhibiting fluid flow into the extraction conduit. When such a condition is suspected, gas sampling is suspended and the valve between the gas analysis system and the intake of the extraction conduit is closed. With the valve closed in order to protect the gas analysis system, a fluid is injected into the extraction conduit from the fluid delivery system.

20 Claims, 6 Drawing Sheets

(51) Int. Cl.
  *E21B 49/08* (2006.01)
  *E21B 21/06* (2006.01)
  *G01N 1/20* (2006.01)
  *G01N 33/28* (2006.01)
  *G01N 1/10* (2006.01)
  *E21B 34/00* (2006.01)

(52) U.S. Cl.
  CPC .......... *E21B 34/00* (2013.01); *G01N 33/2823* (2013.01); *G01N 2001/1025* (2013.01)

(56) References Cited

U.S. PATENT DOCUMENTS

| | | | | |
|---|---|---|---|---|
| 9,765,617 | B2* | 9/2017 | Gosney | .................. E21B 49/08 |
| 2002/0178842 | A1 | 12/2002 | Taylor | |
| 2005/0236050 | A1* | 10/2005 | Manson | ................ F16K 11/072 |
| | | | | 137/625.11 |
| 2008/0115971 | A1 | 5/2008 | Kelleher et al. | |
| 2010/0250142 | A1* | 9/2010 | Zamora | .................. E21B 49/08 |
| | | | | 702/12 |
| 2013/0192360 | A1 | 8/2013 | Jamison et al. | |
| 2013/0270006 | A1 | 10/2013 | Selman et al. | |
| 2013/0319104 | A1* | 12/2013 | Schexnaider | ........ G01N 1/2294 |
| | | | | 73/152.42 |
| 2014/0088874 | A1 | 3/2014 | Selman | |
| 2014/0216176 | A1 | 8/2014 | Kimour | |
| 2017/0198633 | A1* | 7/2017 | Hackett | ................. F02M 37/40 |

OTHER PUBLICATIONS

Supplementary European Search Report issued by the European Patent Office regarding related European Patent Application No. EP 15906843.6, dated Aug. 31, 2018, 7 pages.

* cited by examiner

EXTRACTION CLEANER AND GAS SYSTEM CHECK

PRIORITY

The present application is a U.S. National Stage patent application of International Patent Application No. PCT/US2015/056949, filed on Oct. 22, 2015, the benefit of which is claimed and the disclosure of which is incorporated herein by reference in its entirety.

BACKGROUND

1. Field of the Invention

The present disclosure relates generally to operations related to oil and gas exploration, drilling and production. More particularly, embodiments of the disclosure relate to systems and methods related to monitoring fluids in a well system.

2. Background

Performance of subterranean operations entails various steps, each using a number of devices. Many subterranean operations entail introducing one or more fluids into the subterranean formation. For instance, drilling operations play an important role when developing oil, gas or water wells or when mining for minerals and the like. During the drilling operations, a drill bit passes through various layers of earth strata as it descends to a desired depth. Drilling fluids are commonly employed during the drilling operations and perform several important functions including, but not limited to, removing the cuttings from the well to the surface, controlling formation pressures, sealing permeable formations, minimizing formation damage, and cooling and lubricating the drill bit.

Properties of the drilling fluid are typically monitored during drilling operations. For instance, it is often desirable to accurately measure hydrocarbon gas concentrations of the drilling fluid as it leaves the wellbore. The level of the formation gas in the drilling fluid may affect how the well is to be drilled as well as the safety of the drilling rig and personnel involved. Moreover, the concentration of hydrocarbon gases and other components present in the drilling fluid may be indicative of the characteristics of the formation being drilled and the drilling environment. Accordingly, the analysis of drilling fluids and the changes they undergo during drilling operations may be important to the methods of drilling as well as the efficiency of the drilling operations. Consequently, during drilling, completion and testing of a wellbore, it is desirable to obtain analytical measurements of the fluids that are returned to the surface from the well bore.

In this regard, a gas detection system may include an extraction tube for obtaining analysis samples from returning drilling fluid. The extraction tube extends into the flow path of the drilling fluid and is in fluid communication with a gas extractor. The gas extractor, in turn, is in fluid communication with a gas detector. Since the returning drilling fluids contain particulate matter or solids of various sizes, a portion of the extraction tube extending into the flow path of the drilling fluid may include a screen or filter to minimize clogging within the extraction tube. However, over time, particulate matter will build up on the screen or filter, clogging and impairing extraction of gas samples from the returning drilling fluid flow path.

BRIEF DESCRIPTION OF THE DRAWINGS

The disclosure is described in detail hereinafter on the basis of embodiments represented in the accompanying figures, in which.

DETAILED DESCRIPTION

Detailed Description of the Invention

Figure 1:
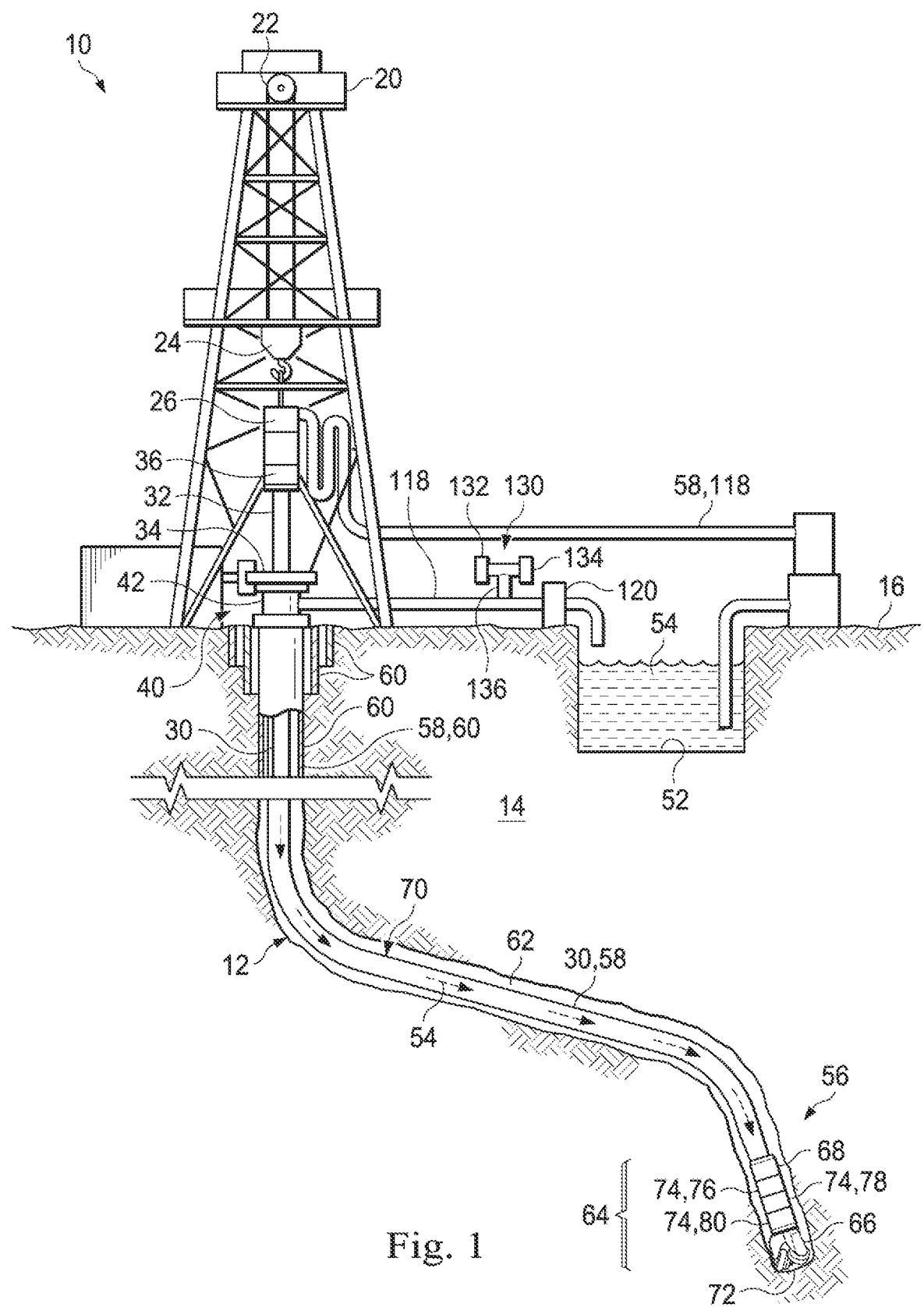
FIG. 1 is a cross-sectional schematic side-view of a drilling system including a gas extraction system in accordance with one or more exemplary embodiments of the disclosure.

The disclosure may repeat reference numerals and/or letters in the various examples or Figures. This repetition is for the purpose of simplicity and clarity and does not in itself dictate a relationship between the various embodiments and/or configurations discussed. Further, spatially relative terms, such as beneath, below, lower, above, upper, uphole, downhole, upstream, downstream, and the like, may be used herein for ease of description to describe one element or feature's relationship to another element(s) or feature(s) as illustrated, the upward direction being toward the top of the corresponding figure and the downward direction being toward the bottom of the corresponding figure, the uphole direction being toward the surface of the wellbore, the downhole direction being toward the toe of the wellbore. Unless otherwise stated, the spatially relative terms are intended to encompass different orientations of the apparatus in use or operation in addition to the orientation depicted in the Figures. For example, if an apparatus in the Figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

Moreover even though a Figure may depict a horizontal wellbore or a vertical wellbore, unless indicated otherwise, it should be understood by those skilled in the art that the apparatus according to the present disclosure is equally well suited for use in wellbores having other orientations including vertical wellbores, deviated wellbores, multilateral wellbores or the like. Likewise, unless otherwise noted, even though a Figure may depict an offshore operation, it should be understood by those skilled in the art that the apparatus according to the present disclosure is equally well suited for use in onshore operations and vice-versa. Further, unless otherwise noted, even though a Figure may depict a cased hole, it should be understood by those skilled in the art that the apparatus according to the present disclosure is equally well suited for use in open hole operations.

Generally, in one or more embodiments, gas sampling of a flow stream in a drilling and production system is conducted. An extraction conduit is utilized to fluidly communicate with the flow stream and deliver a fluid to a gas analysis system. The extraction conduit may include one or more openings, as well as one or more screens or filters adjacent the openings in order to prevent debris from entering the extraction conduit. A parameter of the flow stream, such as a particular gas content or the presence of a bump gas, may be monitored. A change in the parameter may be indicative that debris is inhibiting fluid flow into the extraction conduit. When such a condition is suspected, gas sampling is suspended and a valve between the gas analysis system and the intake or open end of the extraction conduit is closed. With the valve closed in order to protect the gas analysis system, a fluid is injected into the extraction conduit from a fluid source. Preferably, the fluid is injected under pressure, hence the need to close the aforementioned valve in order to prevent damage to the gas analysis system. The injected fluid is utilized to clear or otherwise remove debris from the openings and/or screen. Once the procedure is complete, the valve may be reopened and sampling may continue. Vibrations may be applied to the extraction conduit to assist in debris removal.

Figure 2:
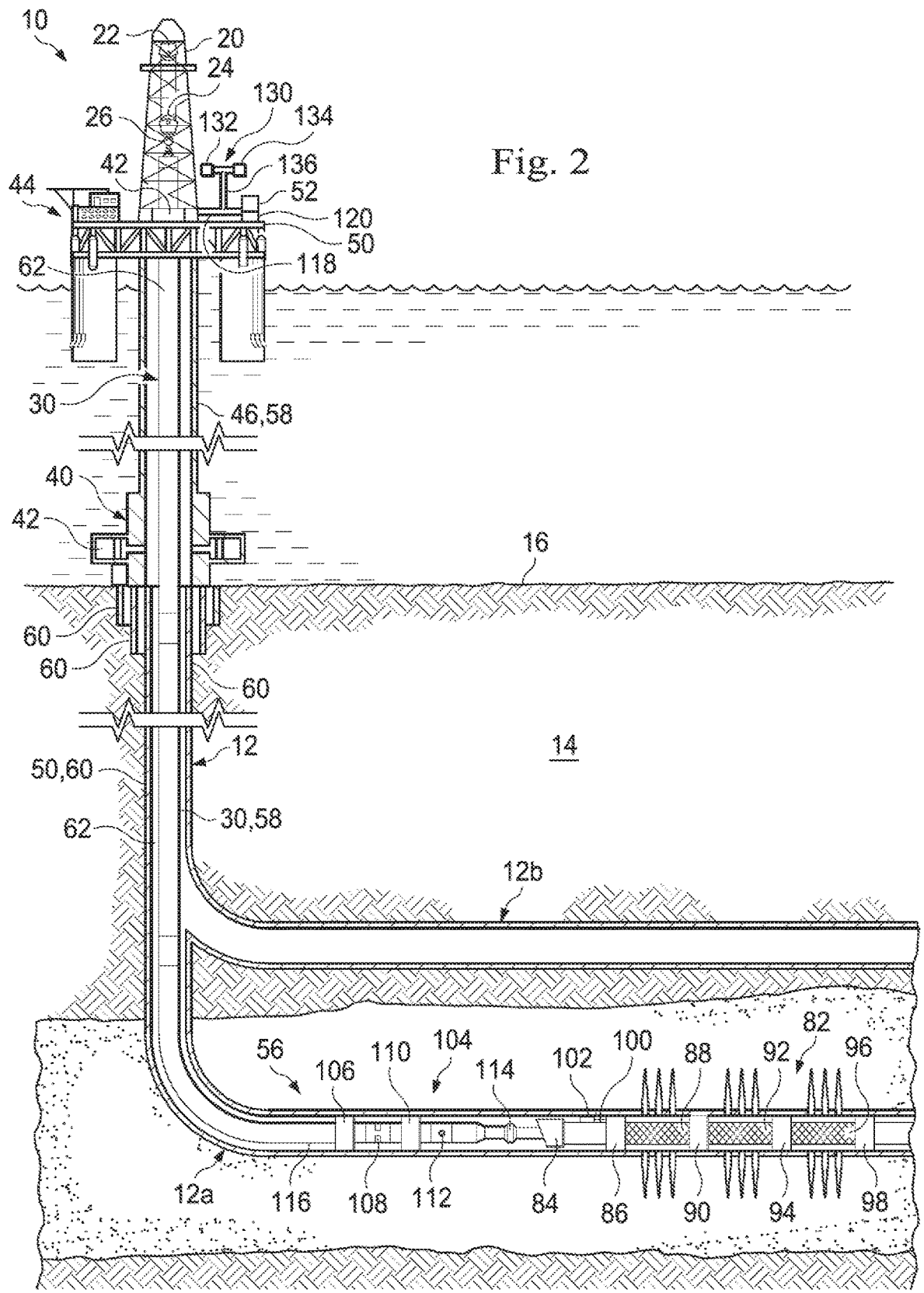
FIG. 2 illustrates an embodiment of a gas extraction system of the disclosure deployed in a marine-based production system.

Turning to FIGS. 1 and 2, shown is an elevation view in partial cross-section of a wellbore drilling and production system 10 utilized to produce hydrocarbons from wellbore 12 extending through various earth strata in an oil and gas formation 14 located below the earth's surface 16. Wellbore 12 may be formed of a single or multiple bores 12a, 12b . . . 12n (illustrated in FIG. 2), extending into the formation 14, and disposed in any orientation, such as the horizontal wellbore 12b illustrated in FIG. 2.

Drilling and production system 10 may include a drilling rig or derrick 20. Drilling rig 20 may include a hoisting apparatus 22, a travel block 24, and a swivel 26 for raising and lowering casing, liner, drill pipe, work string, coiled tubing, production tubing (including production liner and production casing), and/or other types of pipe or tubing strings collectively referred to herein as tubing string 30, or other types of conveyance vehicles, such as wireline, slickline or cable. In FIG. 1, conveyance vehicle 30 is a substantially tubular, axially extending drill string formed of a plurality of drill pipe joints coupled together end-to-end, while in FIG. 2, conveyance vehicle 30 is completion tubing supporting a completion assembly as described below. Drilling rig 12 may include a kelly 32, a rotary table 34, and other equipment associated with rotation and/or translation of tubing string 30 within a wellbore 12. For some applications, drilling rig 18 may also include a top drive unit 36.

Drilling rig 20 may be located proximate to a wellhead 40 as shown in FIG. 1, or spaced apart from wellhead 40, such as in the case of an offshore arrangement as shown in FIG. 2. One or more pressure control devices 42, such as blowout preventers (BOPs) and other equipment associated with drilling or producing a wellbore may also be provided at wellhead 40 or elsewhere in the system 10.

For offshore operations, as shown in FIG. 2, whether drilling or production, drilling rig 20 may be mounted on an oil or gas platform 44, such as the offshore platform as illustrated, semi-submersibles, drill ships, and the like (not shown). Although system 10 of FIG. 2 is illustrated as being a marine-based production system, system 10 of FIG. 2 may be deployed on land. Likewise, although system 10 of FIG. 1 is illustrated as being a land-based drilling system, system 10 of FIG. 1 may be deployed offshore. In any event, for marine-based systems, one or more subsea conduits or risers 46 extend from deck 50 of platform 44 to a subsea wellhead 40. Tubing string 30 extends down from drilling rig 20, through subsea conduit 46 and BOP 42 into wellbore 12.

A working or service fluid source 52, such as a storage tank or vessel, may supply a working fluid 54 pumped to the upper end of tubing string 30 and flow through tubing string 30. Working fluid source 52 may supply any fluid utilized in wellbore operations, including without limitation, drilling fluid, cementious slurry, acidizing fluid, liquid water, steam or some other type of fluid.

Wellbore 12 may include subsurface equipment 56 disposed therein, such as, for example, a drill bit and bottom hole assembly (BHA), a completion assembly or some other type of wellbore tool.

Wellbore drilling and production system 10 may generally be characterized as having a pipe system 58. For purposes of this disclosure, pipe system 58 may include casings, risers, tubing, drill strings, completion or production strings, subs, heads or any other pipes, tubes or equipment that attaches to the foregoing, such as string 30 and conduit 46, as well as the wellbore and laterals in which the foregoing may be deployed. In this regard, pipe system 58 may include one or more casing strings 60 that may be cemented in wellbore 12, such as the surface, intermediate and production casings 60 shown in FIG. 1. An annulus 62 is formed between the walls of sets of adjacent tubular components, such as concentric casing strings 60 or the exterior of tubing string 30 and the inside wall of wellbore 12 or casing string 60, as the case may be.

Where subsurface equipment 56 is used for drilling, conveyance vehicle 30 is a drill string, the lower end of which may include bottom hole assembly 64, which may carry at a distal end a drill bit 66. During drilling operations, weight-on-bit (WOB) is applied as drill bit 66 is rotated, thereby enabling drill bit 66 to engage formation 14 and drill wellbore 12 along a predetermined path toward a target zone. In general, drill bit 66 may be rotated with drill string 30 from rig 20 with a top drive 36 or rotary table 34, and/or with a downhole mud motor 68 within BHA 64. The working fluid 54 is pumped to the upper end of drill string 30 and flows through the longitudinal interior 70 of drill string 30, through bottom hole assembly 64, and exit from nozzles formed in drill bit 66. At bottom end 72 of wellbore 12, drilling fluid 54 may mix with formation cuttings, formation fluids and other downhole fluids and debris. The drilling fluid mixture may then flow upwardly through an annulus 62 to return formation cuttings and other downhole debris to the surface 16.

Bottom hole assembly 64 and/or drill string 30 may include various other tools 74, including a power source 76, mechanical subs 78 such as directional drilling subs, and measurement equipment 80, such as measurement while drilling (MWD) and/or logging while drilling (LWD) instruments, detectors, circuits, or other equipment to provide information about wellbore 12 and/or formation 14, such as logging or measurement data from wellbore 12. Measurement data and other information from tools 74 may be communicated using electrical signals, pressure signals, acoustic signals or other telemetry that can be converted to electrical signals at the rig 20 to, among other things, monitor the performance of drilling string 30, bottom hole assembly 64, and associated drill bit 66, as well as monitor the conditions of the environment to which the bottom hole assembly 64 is subjected.

With respect to FIG. 2 where subsurface equipment 56 is illustrated as completion equipment, disposed in a substantially horizontal portion of wellbore 12 is a lower completion assembly 82 that includes various tools such as an orientation and alignment subassembly 84, a packer 86, a sand control screen assembly 88, a packer 90, a sand control screen assembly 92, a packer 94, a sand control screen assembly 96 and a packer 98.

Extending downhole from lower completion assembly 82 is one or more communication cables 100, such as a sensor or electric cable, that passes through packers 86, 90 and 94 and is operably associated with one or more electrical devices 102 associated with lower completion assembly 82, such as sensors position adjacent the sand control screen assemblies 88, 92, 96 or at the sand face of formation 14, or downhole controllers or actuators used to operate downhole tools or fluid flow control devices. Cable 100 may operate as communication media, to transmit power, or data and the like between lower completion assembly 82 and an upper completion assembly 104.

In this regard, disposed in wellbore 12 at the lower end of tubing string 30 is an upper completion assembly 104 that includes various tools such as a packer 106, an expansion joint 108, a packer 110, a fluid flow control module 112 and an anchor assembly 114.

Extending uphole from upper completion assembly 104 are one or more communication cables 116, such as a sensor cable or an electric cable, which passes through packers 106, 110 and extends to the surface 16. Cable 116 may operate as communication media, to transmit power, or data and the like between a surface controller (not pictured) and the upper and lower completion assemblies 104, 82.

Fluids, such as drilling mud, hydrocarbons, steam and the like, along with solid matter such as cuttings and other debris, returning to surface 16 from wellbore 12 are directed by a flow line 118 to storage tanks 52 and/or processing systems 120, such as shakers, centrifuges and the like.

Shown deployed in FIG. 1 and FIG. 2 in association with wellbore 12 is a gas extraction and sampling system 130. In particular, gas extraction and sampling system 130 is deployed to be in fluid communication with wellbore 12, and generally includes a gas analysis system 132, a fluid pump 134 and an extraction conduit 136 which extraction conduit 136 is in fluid communication with wellbore 12. In one or more embodiments, extraction conduit 136 is in fluid communication with return flow line 118. While gas extraction and sampling system 130 is illustrated as deployed along return flow line 118, gas extraction and sampling system 130 may be deployed anywhere along a fluid flow path of drilling and production system 10, and more specifically anywhere along pipe system 58. For example, extraction conduit 136 may extend into storage tanks 52 or may be positioned to extent into flow lines, or into processing systems 120 or may be positioned to sample working fluid 54 prior to injection into wellbore 12.

Figure 3:
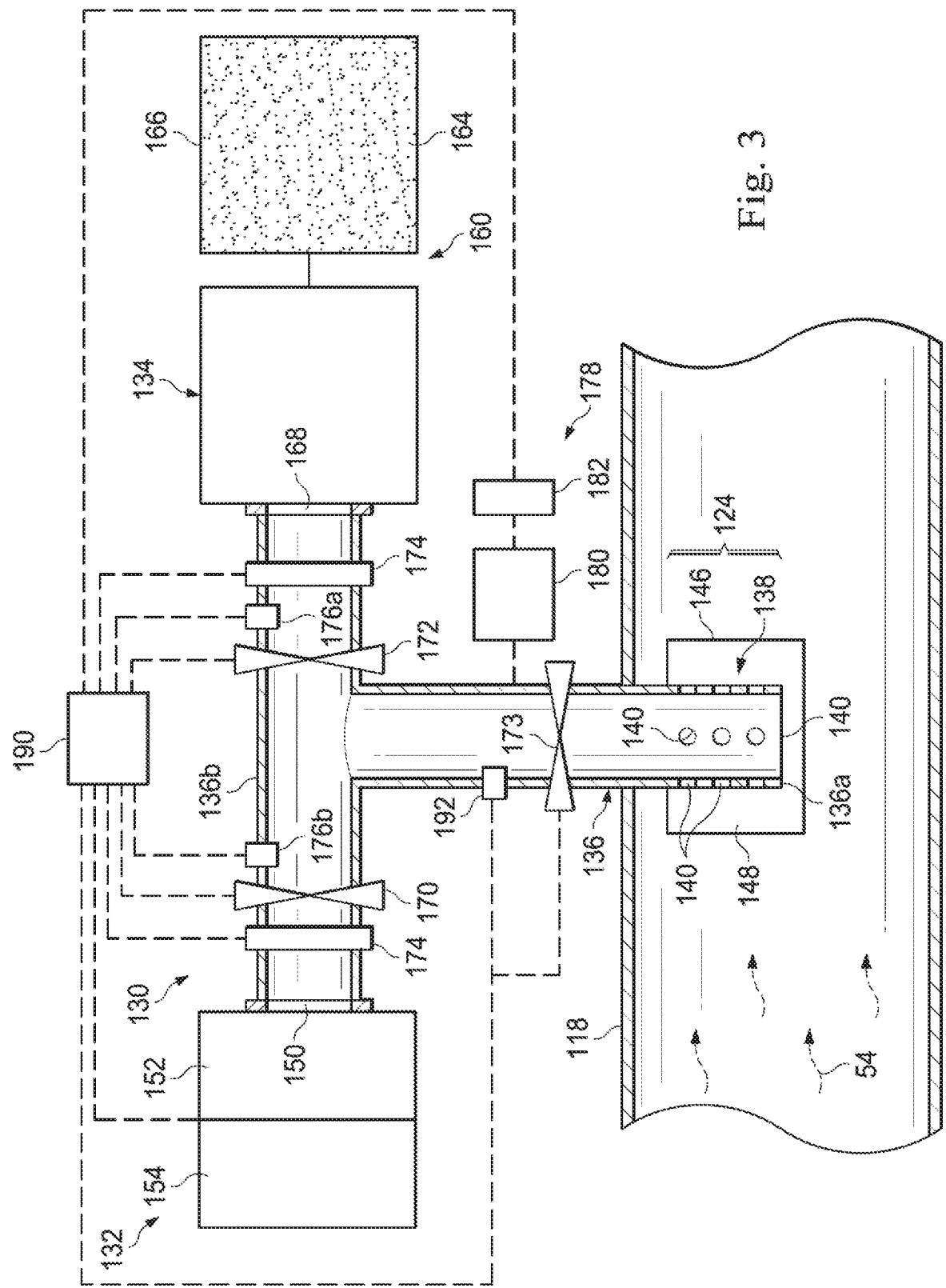
FIG. 3 is a schematic block diagram of a the gas extraction system of FIGS. 1 and 2.

Turning to FIG. 3, an embodiment of gas extraction and sampling system 130 is illustrated in more detail. In the illustrated embodiment, gas extraction and sampling system 130 is disposed to sample gas from the returning wellbore fluids. More specifically, an extraction conduit 136, such as a suction tube or pipe, is shown in fluid communication with return flow line 118. Extraction conduit 136 includes an intake 138 disposed at a first end 136a of extraction conduit 136. Intake 138 has at least one opening 140 in the extraction conduit. In some embodiments, opening 140 may be at the furthest-most end of extraction conduit 136, while in other embodiments, opening 140 may alternatively or additionally be formed in the wall of extraction conduit 136 adjacent first end 136a. In this regard, a plurality of openings 140 may be formed in the wall of extraction conduit 136. In one or more embodiments, the plurality of openings may function as a filter to prevent larger debris from entering extraction conduit 136. In one or more embodiments, such as is illustrated in FIG. 3, a portion 124 of extraction conduit 136 extends into the interior of flow line 118 so that opening 140 is positioned in the flowpath of fluid 54.

In one or more embodiments, a filter 146 is disposed over opening 140. Filter 146 may be a screen or similar porous material to allow liquid to flow through filter 146. As shown in FIG. 3, in some embodiments, filter 146 may be spaced apart from opening(s) 140 so as to form an annular region 148 therebetween.

A gas analysis system 132 is fluidically coupled to extraction conduit 136. Gas analysis system 132 may be coupled to extraction conduit 136 at a second end 136b of extraction conduit 136. In one or more embodiments, the gas analysis system 132 can be an inline, sealed system such as an EAGLE extraction system, a constant volume extractor (CVE) system or a non-sealed degasser system such as a quantitative gas measurement (QGM) system. Gas analysis system 132 includes an inlet 150 in fluid communication with extraction conduit 136. Gas analysis system 132 may include a gas extractor 152 and a gas detector 154.

A fluid delivery system 160 is also fluidically coupled to the extraction conduit 136. Fluid delivery system 160 may be coupled to extraction conduit 136 at second end 136b of extraction conduit 136. Fluid delivery system 160 includes a fluid pump 134 for pumping a fluid 164 from a fluid source 166. In one or more embodiments, fluid 164 may be pressurized. Fluid 164 may be a liquid or gas. In one or more embodiments, fluid 164 is compressed air and fluid source 166 is a storage vessel for gas. Fluid delivery system 160 includes an inlet 168 in fluid communication with extraction conduit 136. In embodiments, fluid 164 is non-compressible or minimally compressible (less than 1% at expected pressures), such as a liquid. In embodiments, fluid 164 may be drilling fluid utilized in the drilling of wellbore 12. In embodiments, fluid 164 may be a non-hydrocarbon or some other fluid that differs from any fluids expected to be returning from wellbore 12.

A first valve 170 is disposed between inlet 150 of gas analysis system 132 and extraction conduit 136. A second valve 172 may be disposed between fluid delivery system 160 and extraction conduit 136. Each valve 170, 172 is movable between a first position in which an associated system 132, 160 is in fluid communication with the extraction conduit 136 and a second position in which fluid communication between the associated system 132, 160 and the extraction conduit 136 is blocked. As will be described below, first valve 170 may be used to isolate gas analysis system 132 from extraction conduit 136 when fluid 136 is injected into extraction conduit 136 in order to clear intake 138.

In one or more embodiments, an additional or third valve 173 may be placed along extraction conduit 136 between ends 136a and 136 b to allow direct fluid passage between source 166 and gas analysis system 132. In operation, valve 173 may be closed for the purpose of verifying that gas analysis system 132 is functioning as desired by introducing fluid 166 into gas analysis system 132. It will be appreciated that third valve 173 may be utilized to isolate gas analysis system 132 from the well system.

In one or more embodiments, gas extraction and sampling system 130 may also include a monitoring device such as a first flow meter or sensor 174 to measure mass or volumetric flow rate of a liquid or a gas 134 from fluid delivery system 160. In one or more embodiments, gas extraction and sampling system 130 may also include a monitoring device such as a second flow meter or sensor 174 or both adjacent gas analysis system 132 to measure mass or volumetric flow rate of a fluid flow to gas analysis system 132. In some embodiments, a sensor 174 is positioned between valve 170 and entry 150 to analysis system 132 in order to provide verification that flow exists between extraction tube and the gas system. If no flow is present, it could be an indication that valve 170 is not functioning properly or that the extraction tube 136 is clogged, which results may be used to trigger an alarm and/or to start a bump test as described herein. In some embodiments, flow meter 174 is a Coriolis meter.

Likewise, in one or more embodiments, gas extraction and sampling system 130 may also include a monitoring device such as a first pressure gauge 176a to measure pressure of a liquid or a gas 134 from fluid delivery system 160. In one or more embodiments, gas extraction and sampling system 130 may also include a monitoring device such as a second pressure gauge 176b to measure pressure of a fluid flow to gas analysis system 132. The system may contain a vacuum gauge 192 to measure the vacuum of the suction tube line as system 132 draws the sample from fluid 54.

In one or more embodiments, gas extraction and sampling system 130 may also include a vibration system 178. Vibration system 178 may include a vibration source 180 coupled to extraction conduit 136 and a vibrator control system 182 for controlling actuation of vibration source 180. Vibration source 180 may be any device that can generate vibrations in conduit 136 when activated including mechanical vibrations, pneumatic vibrations, sonic vibrations and the like. In this regard, in some embodiments, vibration source 180 may be mechanically, pneumatically or acoustically coupled to extraction conduit 136.

Figure 4:
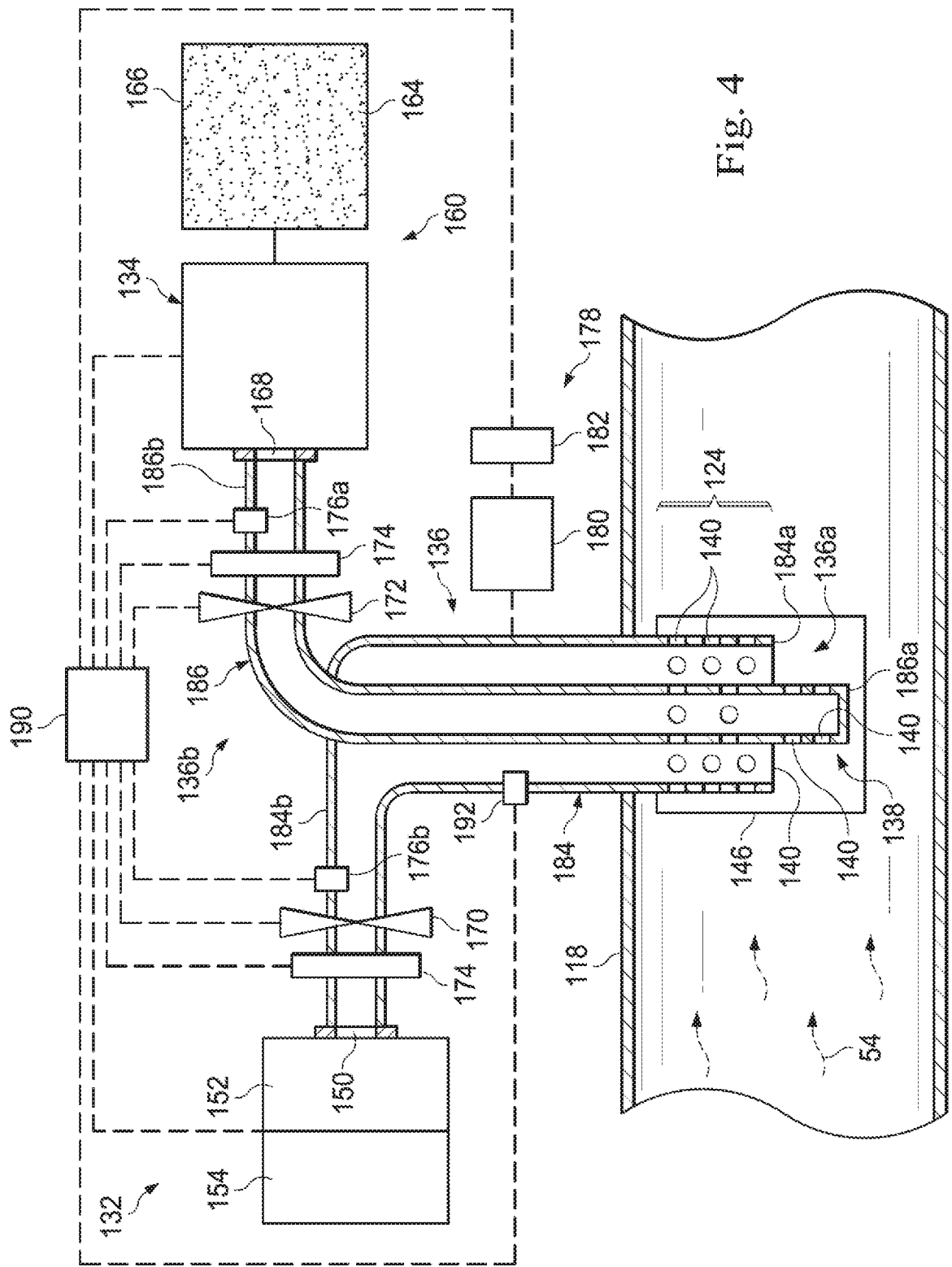
FIG. 4 is a schematic block diagram of another embodiment of the gas extraction system of FIGS. 1 and 2

With reference to FIG. 4, extraction conduit 136 may comprise a first tubular 184 and a second tubular 186 with one tubular at least partially disposed in the other tubular. Each tubular 184, 186 includes a first end 184a, 186a and a second end 184b, 186b, respectively. The first end 184a, 186a of at least one of the tubulars 184, 186 forms the first end 136a of extraction conduit 136. The other first end 184a, 186a of the other tubular 184, 186, as the case may be, may be coextensive with first end 136a or may terminate at a different point. In any event, the second end 184b, 186b of one of the tubulars 184, 186 is in fluid communication with the fluid delivery system 160, while the second end 184b, 186b of the other tubular 184, 186 is in fluid communication with the gas analysis system 132.

In FIG. 4, first tubular 184 is illustrated as the outer tubular and second tubular 186 is disposed therein an inner tubular. Each of the tubulars 184, 186 may include an opening 140. In some embodiments, opening 140 may be at the furthest-most end of a tubular 184, 186, while in other embodiments, opening 140 may alternatively or additionally be formed in the wall of a tubular 184, 186 adjacent the first end 184a, 186a. In this regard, a plurality of openings 140 may be formed in the wall of a tubular 184, 186. In the illustrated embodiment, an opening 140 is formed at the furthest-most end of first tubular 184, while a plurality of openings 140 are formed in the wall of second tubular 186. Also in the illustrated embodiment, first end 186a extends below or spaced apart from first end 184a, although as noted above, the ends 184a, 186a may also terminate adjacent one another or end 186a may terminate above end 184a.

First valve 170 is disposed at second end 184b of first tubular 184. Second valve 172 may be disposed at second end 186b.

Figure 5:
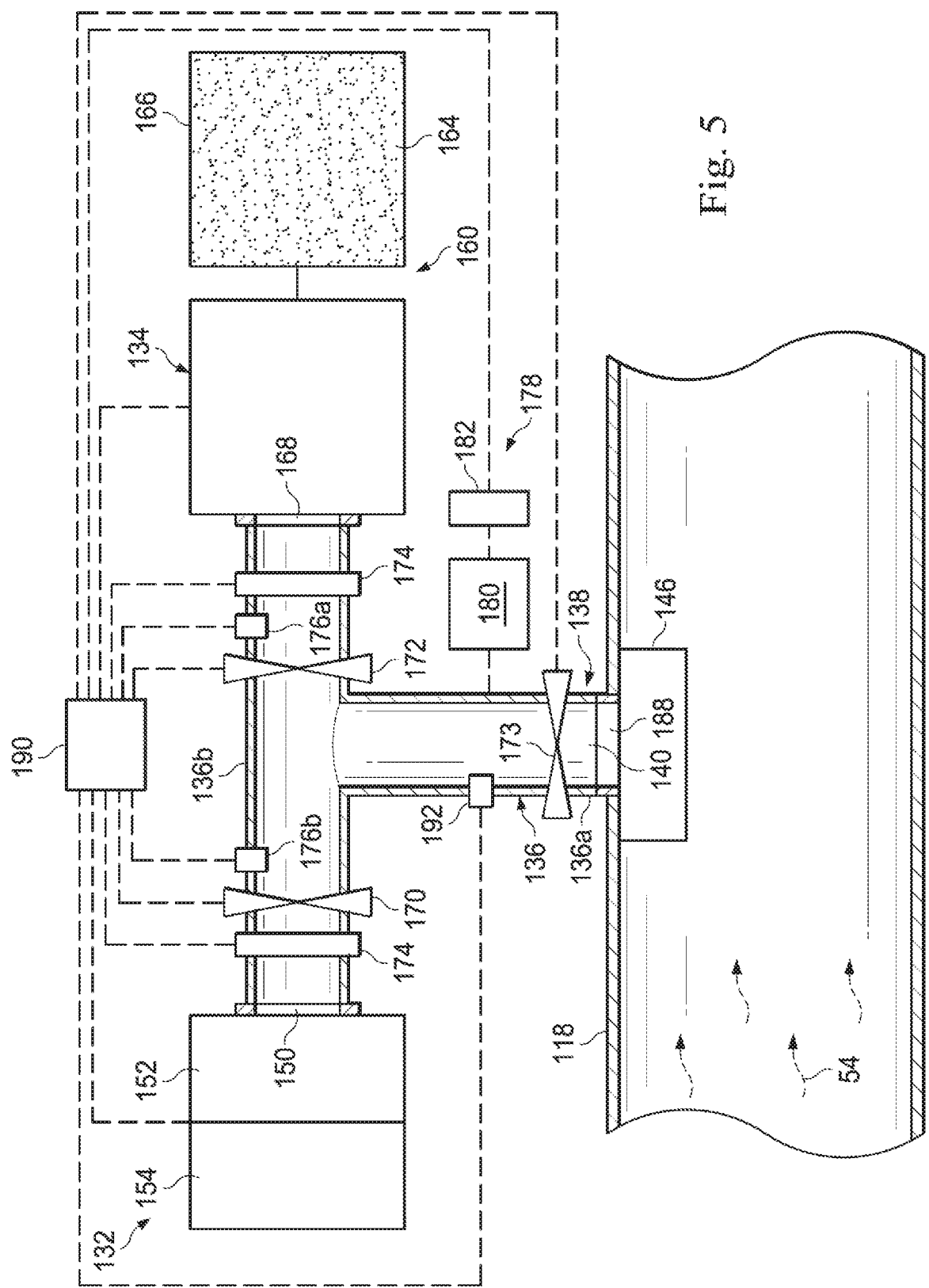
FIG. 5 is a schematic block diagram of another embodiment of the gas extraction system of FIGS. 1 and 2.

In another embodiment illustrated in FIG. 5, flow line 118 includes an opening 188 therein. The first end 136a of extraction conduit 136 is in fluid communication with opening 188, and specifically, opening 140 at the end of extraction conduit 136 is in fluid communication with opening 188 of flow line 118. In this embodiment, a filter 146 is disposed over opening 140. Filter 146 may be a screen or similar porous material to allow liquid to flow through filter 146 or otherwise a grate with a plurality of openings 140 that function as a filter.

Finally, a control system 190 as shown in FIGS. 3, 4 and 5 may be provided to monitor, coordinate and control operations of one or more of the components of gas extraction and sampling system 130, including gas analysis system 132, fluid delivery system 160, fluid pump 134, first valve 170, second valve 172, third valve 173, flow meter or sensor 174, pressure gauge 176, pressure gauge 192, and vibration system 178. Control system 190 may include an alarm which may be activated upon the occurrence a predetermined condition, such as a change or a particular threshold in pressure, flow-rate, gas composition or similar monitored parameter.

Turning to operation of gas extraction and sampling system 130, generally during fluid flow in a wellbore drilling and production system 10, fluid in the pipe system 58 may be sample and analyzed for gas content. Moreover, the components of identified gas may be determined utilizing a gas analysis system such as gas analysis system 132. As described above, however, debris build-up or clogging adjacent intake 138 of the extraction conduit 136 can inhibit gas detection or otherwise skew result, such as indicating detected gas levels from a zone in the wellbore are less than the actual gas levels from the zone. Debris build-up or clogging can be particularly troublesome in flow lines of fluids returning from the wellbore, where formation cuttings, mud weighting material and other particulate solids may be entrained in the returning fluids. Thus, in order to ensure uninhibited flow from a flow line to the extraction conduit, either at predetermined time intervals or when clogging or build-up is suspected, first valve 170 is closed, second valve 172 is opened and fluid delivery system 160 is used to inject or otherwise deliver a flow of pressurized fluid into extraction conduit 136 and in particular, to intake 138. Because first valve 170 is closed, the pressurized fluid will be forced out of extraction conduit 136, removing any debris that may have accumulated at intake 138. To the extent a filter 146 is disposed about intake 138, the pressurized fluid will be forced outward through filter 146 and into the flow stream of flow line 118. In so doing, debris on filter 146 will be removed, thus improving fluid flow into extraction conduit 136. It will be appreciated that because first valve 170 is closed, gas analysis system 132 is also isolated and protected from the pressurized fluid which might otherwise damage gas analysis system 132. Fluid 164 from a fluid source 166 may be delivered by fluid pump 134 as a steady stream or in intermittent bumps or slugs. Once the intake 138 and any filter 146 have been satisfactorily cleared of debris, second valve 172 is closed, first valve 170 is opened and gas monitoring can continue. For example, the screen would be considered satisfactorily clear when there is a change in the flow rate of the Coriolis meter 174. When the system is clogged, the flow rate would be minimal or zero if completely clogged. The pressure should be high, when flow begins and continues to increase to a normal state due to unclogging of the screen, the pressure will reduce and normalize due to the increased flow rate.

Figure 6:
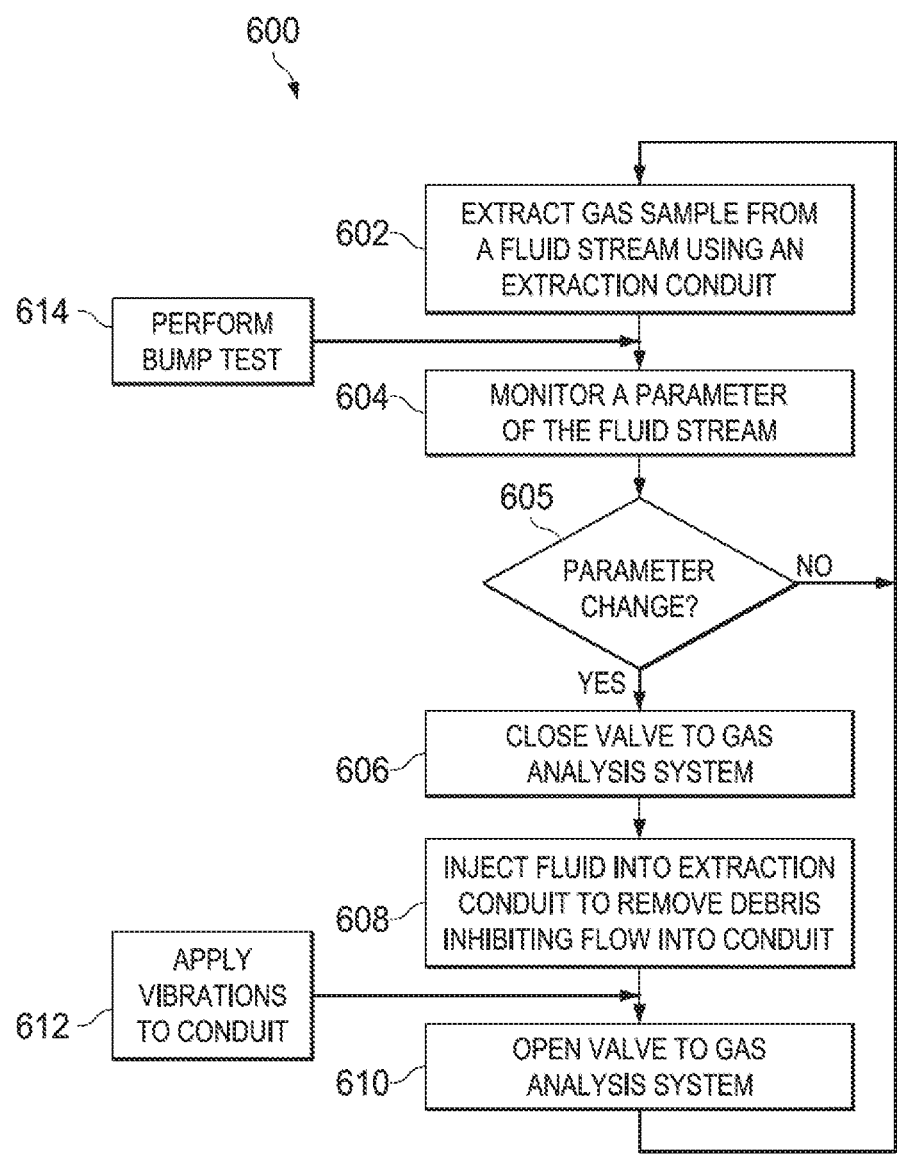
FIG. 6 is a flowchart illustrating a gas extraction method for use with hydrocarbon drilling and extraction.

The foregoing is illustrated in FIG. 6, where method 600 of monitoring fluids of a wellbore system is shown. In a first step 602, an extraction conduit is utilized to extract a gas sample from a fluid stream in a flow line associated with the wellbore. More specifically, liquid from a flow line is drawn into gas analysis system 132, where gas is isolated from the liquid for analysis. During sampling of gas in a flow line, in step 604, one or more parameters may be monitored as an indicator that debris build-up or clogging of flow into extraction conduit is occurring. In some embodiments, the primary parameters would be the flow rate measured by the Coriolis sensor and the pressure measured by the pressure sensor. In the event that no change in the parameter is observed or otherwise in the event no debris build-up or clogging of the flow extraction conduit is suspected, sampling may continue in accordance with step 602.

In the event debris build-up or clogging of flow into extraction conduit is suspected, as may be evidenced by a change in parameters as shown by 605, in step 606, the valve between the gas analysis system and the extraction conduit is closed in order to isolate gas analysis system from the extraction conduit. With the valve closed, in step 608, a fluid is injected into the extraction conduit. In one or more embodiments, the fluid is injected at a point adjacent the inlet or opening of the extraction conduit into which the fluids flow from the flow line. In one or more embodiments, the injected fluid is pressurized to deliver a greater amount of energy to the region of the build-up or clog in order to clear the area of debris that is inhibiting flow into the extraction conduit. In this regard, the pressurized fluid may clear debris from openings in the extraction conduit, and in addition, or in the alternative, clear debris from any filter disposed about the extraction conduit. Once the pressurized fluid has been injected in order to remove debris, in step 610, the valve to the gas analysis system may be reopened and sampling can continue, as at step 602.

To further enhance cleaning of the debris, vibrations may be applied to the extraction conduit 136 and/or filter 146. More specifically, as desired, a vibration source coupled to the extraction conduit 136 may be activated to apply vibrations to the extraction conduit 136 and/or filter 146. In this regard, vibration source may apply vibrations before, after or during application of the pressurized fluid to extraction conduit 136. Thus, in a step 612, vibrations may be applied to extraction conduit 136.

In one or more embodiments, the foregoing cleaning method may be used in conjunction with a bump test performed on wellbore drilling and production system 10. More specifically, a bump test is a common method for testing and evaluating the operation of gas sensors, gas analysis systems and the like, such as gas analysis system 132, wherein the equipment under investigation is briefly exposed to a gas released into a circulating fluid stream of wellbore drilling and production system 10. The gas is typically selected to have a property that is not likely to be found in gases that may be included in the returning hydrocarbon flowstream of flow line 118. As such, gas analysis system 132 should readily identify the bump test gas. To the extent the gas analysis system 132 does not identify the bump test gas, the above mentioned cleaning procedure may be performed to ensure that the results are not due to a clogged opening 140 or filter 146 of extraction conduit 136. Thus, in 614, a bump test may be conducted during gas sampling in step 602. In some embodiments, the bump test may include releasing a gas into the flow line 118 and then sampling the fluid stream in the flow line 118 utilizing the extraction conduit 136. Thus, the bump test gas is injected upstream of the extraction conduit 136. In this embodiment, the failure of the gas analysis system 132 to detect the bump test gas may be indicative of clogging or debris inhibiting flow into the extraction conduit and thus, function as a trigger for the cleaning procedure described herein.

In other embodiments, the bump test gas may be released directly into the extraction conduit 136. In some embodiments, fluid 164 may be used as the bump test gas, while in other embodiments, a separate source of bump test gas may be utilized. In this embodiment, where one suspects clogging or debris inhibiting flow into the extraction conduit, operation of the gas analysis system 132 can be verified. Specifically, at predetermined intervals or when intake 138 and/or filter 146 are suspected of being clogged, the fluid delivery system 160 may be utilized to perform both the bump test and the above-described cleaning. In such case, second valve 172 is opened and fluid delivery system 160 is used to inject or otherwise deliver gas into extraction conduit 136 and in particular, into any liquid adjacent intake 138. In some embodiments, the pressure used to deliver the fluid 166, such as a noble gas, would be reduced to prevent damage to the gas analysis system 132. The targeted range would be based on the normal operating range when the system is operating without a clog. In any event, because first valve 170 is open, fluid gas analysis system 132 should detect the released gas. In the case where it is verified that gas analysis system 132 is functioning properly, then first valve 170 is closed, second valve 172 is opened and fluid delivery system 160 is used to inject or otherwise deliver a flow of pressurized fluid, which may be the same as the injected bump test gas, into extraction conduit 136 and in particular, to a point adjacent intake 138. Because first valve 170 is closed, the pressurized fluid will be forced out of extraction conduit 136, removing any debris that may have accumulated at intake 138. To the extent a filter 140 is disposed adjacent or in proximity extraction conduit 136, the pressurized fluid will be forced outward through filter 140 and into the flow stream of flow line 118. In so doing, debris on filter 140 will be removed, thus improving fluid flow into extraction conduit 136. It will be appreciated that because first valve 170 is closed, gas analysis system 132 is also isolated and protected from the pressurized fluid which might otherwise damage gas analysis system 132. Fluid 164 from a fluid source 166 may be delivered by fluid pump 134 as a steady stream or in intermittent bumps or slugs. Once the intake 138 and any filter 140 have been satisfactorily cleared of debris, second valve 172 is closed, first valve 170 is opened and gas monitoring can continue as at step 602.

In yet another embodiment, the bump test gas may be released directly into the extraction conduit 136. In this embodiment, where one suspects clogging or debris inhibiting flow into the extraction conduit, operation of the gas analysis system 132 can be verified. Specifically, at predetermined intervals or when intake 138 and/or filter 146 are suspected of being clogged, the fluid delivery system 160 may be utilized to perform both the bump test and the above-described cleaning. In such case, second valve 172 is opened and third valve 173 is closed and fluid delivery system 160 is used to inject or otherwise deliver gas into extraction conduit 136 and in particular, into any liquid adjacent intake 138. The pressure and flow rate of the fluid or gas can be adjusted to operate within the normal operating range of the gas detection system to prevent damage. Because first valve 170 is open, fluid gas analysis system 132 should detect the released gas. The situation provides added advantage of verifying that the gas analysis system is working along with all of the sensor in the closed loop system. For example, the Coriolis meter and pressure meter operation can be verified for proper function, this provides the uses with a system verification test and a way to calibrate the system while in operation at predetermined intervals or during a situation that the system may not be functioning properly. If the system in the working correctly and then the operator can proceed may choose to clear the clogged lines by closing valve 170, opening third valve 173 and open second valve 172 and use the fluid delivery system 160 to inject or otherwise deliver a flow of pressurized fluid, which may be the same as the injected bump test gas, into extraction conduit 136 and in particular, to a point adjacent intake 138. Because first valve 170 is closed and the third valve 173 is open, the pressurized fluid will be forced out of extraction conduit 136, removing any debris that may have accumulated at intake 138. To the extent a filter 146 is disposed adjacent or in proximity extraction conduit 136, the pressurized fluid will be forced outward through filter 146 and into the flow stream of flow line 118. In so doing, debris on filter 146 will be removed, thus improving fluid flow into extraction conduit 136. It will be appreciated that because first valve 170 is closed, gas analysis system 132 is also isolated and protected from the pressurized fluid which might otherwise damage gas analysis system 132. Fluid 164 from a fluid source 166 may be delivered by fluid pump 134 as a steady stream or in intermittent bumps or slugs. Once the intake 138 and any filter 146 have been satisfactorily cleared of debris, second valve 172 is closed, first valve 170 is opened and gas monitoring can continue as at step 602.

In some embodiments, the fluid 164 is non-compressible, such as a liquid, since transfer of energy for clearing of debris or a blockage would be higher than for a compressible gas.

In one or more embodiments of step 604, gas levels may be monitored by gas analysis system 132 and when a predetermined decrease or drop-off in the gas levels is detected, then the cleaning procedure described above may be implemented. For example, a particular parameter of gas, such as concentration or ratio to secondary gas, extracted from flow line 118 may be monitored or measured. A change in the parameter or a particular upper or lower threshold with respect to the monitored or measured parameter would indicate a possible build-up of debris, and thus, the cleaning procedure described could be implemented.

In one or more embodiments of step 604, a flow meter or sensor 174, such as a Coriolis meter, may be used to measure mass or volumetric flow rate of a fluid 164 introduced from fluid delivery system 160. In the event of a blockage of intake 138 and/or filter 146, then measured mass or volumetric flow rate at gas analysis system 132 would be substantially the same or only marginally different than measured mass or volumetric flow rate from fluid delivery system 160, whereas if there is no blockage, then a greater difference in measure mass or volumetric flow rate between sensor 174 and gas analysis system 132 would exist. Thus, in some embodiments mass or volumetric flow rate of fluid 164 is measured as a first measurement as fluid 164 is injected or introduced into extraction conduit 136. Likewise, mass or volumetric flow rate of fluid flowing into gas analysis system 132 is measured as a second measurement. Preferably the second measurement occurs when first valve 170 is open. In any event, a difference between the two measured quantities of less than a predetermined threshold indicates a blockage of flow into intake 138 and/or through any filter 146. In such case, the above-described cleaning procedures may be implemented.

In one or more embodiments of step 604, pressure gauge 176 may be used to measure pressure of a fluid 164 introduced from fluid delivery system 160. In the event of a blockage of intake 138 and/or filter 146, then measure pressure at gas analysis system 132 would be substantially the same or only marginally different than measured pressure at fluid delivery system 160, whereas if there is no blockage, then a greater difference in measure measured pressure between senor 146 and gas analysis system 132 would exist. Thus, in some embodiments pressure of fluid 164 is measured as a first measurement as fluid 164 is injected or introduced into extraction conduit 136. Likewise, pressure of fluid at gas analysis system 132 or at first valve 170 is measured as a second measurement. In some embodiments, the second measurement occurs when first valve 170 is closed, while in other embodiments the second measurement occurs when first valve 170 is open. In any event, a difference between the two measured quantities of less than a predetermined threshold indicates a blockage of flow into intake 138 and/or through any filter 146. In such case, the above-described cleaning procedures may be implemented.

It will be appreciated that any of the foregoing procedures for detecting or identifying a blockage of flow into intake 138 and/or through any filter 146 may be implemented periodically utilizing a control system 190. In such case, a warning may be issued, such as activating an audible or visible alarm, and cleaning procedures as described herein may be automatically implemented by control system 190. In some embodiments, the alarm may be generated if any of the sensors detect "no value" or a value set outside a predetermined range or below a predetermined threshold.

Thus, a fluid extraction apparatus for extracting gas from a fluid flowline has been described. Embodiments of a gas extraction apparatus may generally include an extraction conduit with an intake disposed at a first end of the extraction conduit, the first end of the extraction conduit disposed in fluid communication with the hydrocarbon flowline; a gas analysis system fluidically coupled to the extraction conduit; a fluid delivery system fluidically coupled to the extraction conduit; and a first valve disposed between the gas analysis system and the extraction conduit, the first valve movable between a first position in which the gas analysis system is in fluid communication with the extraction conduit and a second position in which fluid communication between the gas analysis system and the extraction conduit is blocked. Likewise, another embodiment of a fluid extraction apparatus has been described and may generally include an extraction conduit with an intake comprising at least one opening disposed at a first end of the extraction conduit, the first end of the extraction conduit disposed in fluid communication with the hydrocarbon flowline; a gas analysis system fluidically coupled to the extraction conduit; a fluid delivery system fluidically coupled to the extraction conduit; a first valve disposed between the gas analysis system and the extraction conduit, the first valve movable between a first position in which the gas analysis system is in fluid communication with the extraction conduit and a second position in which fluid communication between the gas analysis system and the extraction conduit is blocked; a first monitoring device disposed between the fluid delivery system and the first end of the extraction conduit; and a filter disposed adjacent the at least one opening.

For any of the foregoing embodiments, the apparatus or system may include any one of the following elements, alone or in combination with each other: the intake has at least one opening in the extraction conduit; at least one opening is at the furthest-most end of extraction conduit; at least one opening is formed in a wall of extraction conduit adjacent first end; the intake has a plurality of openings formed in a wall of extraction conduit; a filter is disposed about a portion of the first end of extraction conduit; a filter is a screen or similar porous material; a filter is spaced apart from opening(s) to form an annular region therebetween; a gas analysis system is coupled to extraction conduit at a second end of extraction conduit; a gas analysis system is an inline a sealed system; a gas analysis system is a constant volume extractor (CVE) system; a gas analysis system is a quantitative gas measurement (QGM) system; a gas analysis system comprises a gas extractor and a gas detector, a fluid delivery system is coupled to extraction conduit at a second end of extraction conduit; a fluid delivery system comprises a fluid pump, a fluid source and an injection fluid within the fluid source; an injection fluid is pressurized; an injection fluid is non-compressible; an injection fluid is a liquid; an injection fluid is a gas; an injection fluid is compressed air; an injection fluid is drilling fluid; a mass or volumetric flow rate monitoring device adjacent the fluid delivery system; a mass or volumetric flow rate monitoring device adjacent the gas analysis system; a mass or volumetric flow rate monitoring device is a Coriolis meter; a pressure monitoring device adjacent the fluid delivery system; a pressure monitoring device adjacent the gas analysis system; a vibration system coupled to extraction conduit; the extraction conduit comprises a first tubular at least partially disposed inside a second tubular, each tubular having a first and second end; the first end of one of the tubulars extends beyond the first end of the other tubular; the first end of the first tubular extends beyond the first end of the second tubular, the first end of the second tubular extends beyond the first end of the first tubular, the second end of one tubular is in fluid communication with the fluid delivery system and the second end of the other tubular is in fluid communication with the gas analysis system; each of the first and second tubulars comprises an opening adjacent the first ends of the tubulars; at least one tubular comprises a plurality of openings adjacent the first end of the tubular, the flowline comprises includes an opening therein, wherein said opening at the end of extraction conduit is in fluid communication with the flowline opening and a filter is disposed over said extraction conduit opening; a second valve disposed between the fluid delivery system and the extraction conduit, the second valve movable between a first position in which the fluid delivery system is in fluid communication with the extraction conduit and a second position in which fluid communication between the fluid delivery system and the extraction conduit is blocked; a monitoring device disposed between the fluid delivery system and the first end of the extraction conduit; a monitoring device is a flow sensor, a monitoring device is a pressure sensor; the extraction conduit intake comprises an at least one opening in the extraction conduit and a filter disposed over the at least one opening; a filter comprises a screen; a second monitoring device disposed between the extraction conduit and the gas analysis system; first and second monitoring devices are the same type of monitoring devices; the first end of the extraction conduit extends into an interior of the flow line; a valve disposed between the first end of the extraction conduit and the second end of the extraction conduit and movable between a first position in which the gas analysis system is in fluid communication a flow line and a second position in which fluid flow between a flow line and is blocked.

A method of extracting gas from fluids of a wellbore system has been described. Embodiments of the gas extraction method may include utilizing an extraction conduit to extract gas from a hydrocarbon flow line associated with the wellbore; closing a valve to interrupt flow between the extraction conduit and a gas analysis system in fluid communication with the extraction conduit; and injecting a fluid into the extraction conduit. Other embodiments of a method of gas extraction may include utilizing an extraction conduit to extract gas from a hydrocarbon flow line associated with the wellbore; monitoring a parameter of the extracted gas; when a predetermined parameter threshold of the extracted gas is reached, suspending gas extraction; closing a valve to interrupt flow between the extraction conduit and a gas analysis system in fluid communication with the extraction conduit; and injecting a fluid into the extraction conduit.

For the foregoing embodiments, the method may include any one of the following steps, alone or in combination with each other: isolating the gas analysis system from the extraction conduit; injecting fluid at a point adjacent the inlet or opening of the extraction conduit; injecting a pressurized fluid into the extraction conduit; utilizing pressurized fluid injected into an extraction conduit to clear debris from openings in the extraction conduit; utilizing pressurized fluid injected into an extraction conduit to clear debris from any filter disposed about the extraction conduit; applying vibrations to the extraction conduit; injecting a bump test gas upstream of the extraction conduit and sampling fluid utilizing the extraction conduit in order to monitor for the bump test gas; injecting a bump test gas within the extraction conduit and sampling fluid within the extraction conduit in order to monitor for the bump test gas; injecting a bump test gas at predetermined intervals; utilizing bump test gas to clean the extraction conduit; utilizing bump test gas to clean a filter about the extraction conduit; utilizing a bump test gas to improve fluid flow into the extraction conduit; injecting a bump test gas into the extraction conduit prior to isolating the gas analysis system in fluid communication with the extraction conduit in order to evaluate operation of the gas analysis system; closing a valve to isolate the gas analysis system from fluid communication with the extraction conduit; and, after closing the valve, injecting a bump test gas into the extraction conduit to enhance flow into the extraction conduit from the flow line; monitoring gas levels of fluid within the extraction conduit; and utilizing a predetermined decrease or drop-off in the monitored gas levels to predict the presence of debris adjacent openings in the extraction conduit; utilizing a Coriolis meter to measure mass or volumetric flow rate of an injection fluid introduced into the extraction conduit; utilizing a Coriolis meter to measure a first mass or volumetric flow rate of an injection fluid introduced into the extraction conduit; utilizing a Coriolis meter to measure a second mass or volumetric flow rate of fluid flowing from the extraction conduit into a gas analysis system; and utilizing the difference between the first and second measurements to predict the presence of debris adjacent openings in the extraction conduit; opening the first valve prior to utilizing a Coriolis meter to measure a mass or volumetric flow rate of fluid flowing from the extraction conduit into a gas analysis system; utilizing a pressure monitor to measure pressure of an injection fluid introduced into the extraction conduit; utilizing a pressure monitor to measure a first pressure of an injection fluid introduced into the extraction conduit; utilizing a pressure monitor to measure a second pressure of fluid in the extraction conduit adjacent a gas analysis system; and utilizing the difference between the first and second measurements to predict the presence of debris adjacent openings in the extraction conduit; closing the first valve prior to utilizing a pressure monitor to measure a pressure of fluid in the extraction conduit adjacent a gas analysis system; injecting comprises introducing a fluid into the extraction conduit under pressure; the injected fluid is a liquid; forcing injected fluid out of an extraction conduit intake and into the hydrocarbon flow line; forcing comprises passing the fluid through a filter disposed over an opening in the extraction conduit in order to remove debris accumulated on the filter; periodically injecting a fluid into the extraction conduit and monitoring a parameter of the injected fluid in the extraction conduit; and when a predetermined parameter threshold is reached, suspending gas extraction and cleaning the extraction conduit; conducting a bump test to evaluate the accumulation of debris inhibiting gas extraction through the extraction conduit; monitoring a parameter of the extracted gas; and when a predetermined parameter threshold of the extracted gas is reached, suspending gas extraction and cleaning the extraction conduit; cleaning comprises utilizing a pressurized fluid injected into the extraction conduit to remove debris inhibiting gas extraction through the extraction conduit; cleaning comprises vibrating the extraction conduit to remove debris inhibiting gas extraction through the extraction conduit; activating an alarm when then the predetermined parameter threshold is reached; blocking fluid communication between the gas analysis system and the intake to the extraction conduit, injecting a test fluid within the extraction conduit and utilizing the test fluid to evaluate operation of the gas analysis system.

What is claimed is:

1. A fluid extraction apparatus for extracting gas from a fluid flowline, the gas extraction apparatus comprising:
    an extraction conduit with an intake disposed at a first end of the extraction conduit, the first end of the extraction conduit disposed in fluid communication with the fluid flowline;
    a gas analysis system fluidically coupled to the extraction conduit;
    a fluid delivery system fluidically coupled to the extraction conduit and configured to deliver a fluid through the extraction conduit and into the fluid flowline; and
    a first valve disposed between the gas analysis system and the extraction conduit, the first valve movable between a first position in which the gas analysis system is in fluid communication with the extraction conduit and a second position in which fluid communication between the gas analysis system and the extraction conduit is blocked.

2. The apparatus of claim 1, further comprising a vibration system coupled to the extraction conduit.

3. The apparatus of claim 1, further comprising a second valve disposed between the fluid delivery system and the extraction conduit, the second valve movable between a first position in which the fluid delivery system is in fluid communication with the extraction conduit and a second position in which fluid communication between the fluid delivery system and the extraction conduit is blocked.

4. The apparatus of claim 1, further comprising a monitoring device disposed between the fluid delivery system and the first end of the extraction conduit.

5. The apparatus of claim 4, wherein the monitoring device is a flow sensor and/or a pressure sensor.

6. The apparatus of claim 4, further comprising a second monitoring device disposed between the extraction conduit and the gas analysis system.

7. The apparatus of claim 6, wherein the first and second monitoring devices are the same type of monitoring devices.

8. The apparatus of claim 1, wherein the intake comprises an at least one opening in the extraction conduit and a filter disposed over the at least one opening, wherein the filter comprises a screen.

9. The apparatus of claim 1, wherein the first end of the extraction conduit extends into an interior of the flowline.

10. A fluid extraction apparatus for extracting gas from a hydrocarbon flowline, the gas extraction apparatus comprising:
    an extraction conduit with an intake comprising at least one opening disposed at a first end of the extraction conduit, the first end of the extraction conduit disposed in fluid communication with the hydrocarbon flowline;
    a gas analysis system fluidically coupled to the extraction conduit;
    a fluid delivery system fluidically coupled to the extraction conduit and configured to deliver a fluid through the extraction conduit and into the hydrocarbon flowline;
    a first valve disposed between the gas analysis system and the extraction conduit, the first valve movable between a first position in which the gas analysis system is in fluid communication with the extraction conduit and a second position in which fluid communication between the gas analysis system and the extraction conduit is blocked;
    a first monitoring device disposed between the fluid delivery system and the first end of the extraction conduit; and
    a filter disposed adjacent the at least one opening.

11. The apparatus of claim 10, further comprising a second valve disposed between the fluid delivery system and the extraction conduit, the second valve movable between a first position in which the fluid delivery system is in fluid communication with the extraction conduit and a second position in which fluid communication between the fluid delivery system and the extraction conduit is blocked; and
    a second monitoring device disposed adjacent the first valve and the gas analysis system;
    wherein the extraction conduit comprises a first tubular at least partially disposed inside a second tubular, each tubular having a first and second end, where the second end of one tubular is in fluid communication with the fluid delivery system and the second end of the other tubular is in fluid communication with the gas analysis system and each of the first and second tubulars comprises an opening adjacent the first ends of the tubulars.

12. The apparatus of claim 11, further comprising a vibration system coupled to the extraction conduit.

13. A method of extracting gas from fluids of a wellbore system, method comprising:
    utilizing an extraction conduit to extract gas from a hydrocarbon flowline associated with the wellbore;
    closing a valve to interrupt flow between the extraction conduit and a gas analysis system in fluid communication with the extraction conduit; and
    injecting a fluid into the extraction conduit.

14. The method of claim 13, wherein injecting comprises introducing a fluid into the extraction conduit under pressure, wherein the fluid is a liquid.

15. The method of claim 14, further comprising forcing the fluid out of an extraction conduit intake and into the hydrocarbon flowline, wherein forcing comprises passing the fluid through a filter disposed over an opening in the extraction conduit in order to remove debris accumulated on the filter.

16. The method of claim 13, further comprising periodically injecting a fluid into the extraction conduit and monitoring a parameter of the injected fluid in the extraction conduit;

and when a predetermined parameter threshold is reached, suspending gas extraction and cleaning the extraction conduit.

17. The method of claim 16, further comprising conducting a bump test to evaluate the accumulation of debris inhibiting gas extraction through the extraction conduit.

18. The method of claim 13, further comprising monitoring a parameter of the extracted gas; and when a predetermined parameter threshold of the extracted gas is reached, suspending gas extraction and cleaning the extraction conduit.

19. The method of claim 16, wherein cleaning comprises utilizing a pressurized fluid injected into the extraction conduit to remove debris inhibiting gas extraction through the extraction conduit.

20. The method of claim 16, further comprising activating an alarm when then the predetermined parameter threshold is reached.

* * * * *